United States Patent
Harvey et al.

(10) Patent No.: US 9,658,137 B2
(45) Date of Patent: May 23, 2017

(54) MAGNETICALLY-INDUCED SOLID-PHASE MICROEXTRACTION FIBER ACTUATION SYSTEM FOR QUANTITATIVE HEADSPACE AND LIQUID SAMPLING

(71) Applicants: Chris Harvey, French Camp, CA (US); Jerry Carter, Livermore, CA (US); David M. Chambers, Johns Creek, GA (US)

(72) Inventors: Chris Harvey, French Camp, CA (US); Jerry Carter, Livermore, CA (US); David M. Chambers, Johns Creek, GA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 388 days.

(21) Appl. No.: 14/308,503

(22) Filed: Jun. 18, 2014

(65) Prior Publication Data
US 2014/0366651 A1    Dec. 18, 2014

Related U.S. Application Data

(60) Provisional application No. 61/836,581, filed on Jun. 18, 2013.

(51) Int. Cl.
| | | |
|---|---|---|
| *G01N 1/40* | (2006.01) | |
| *G01N 1/10* | (2006.01) | |
| *G01N 30/00* | (2006.01) | |

(52) U.S. Cl.
CPC .............. *G01N 1/10* (2013.01); *G01N 1/405* (2013.01); *G01N 2030/009* (2013.01)

(58) Field of Classification Search
None
See application file for complete search history.

(56) References Cited

U.S. PATENT DOCUMENTS 7,131,341 B2 *   11/2006   Wareham et al. ......... 73/864.71
8,006,540 B2 *    8/2011   Degli Esposti et al. ..... 73/23.41

FOREIGN PATENT DOCUMENTS

| EP | 1924835 | 5/2008 |
|---|---|---|
| EP | 2485035 | 8/2012 |

(Continued)

OTHER PUBLICATIONS

Globig, D. and C. Weickhardt (2005). "Fully automated in-tube solid-phase microextraction for liquid samples coupled to gas chromatography." Analytical and Bioanalytical Chemi.

(Continued)

*Primary Examiner* — Robert R Raevis
(74) *Attorney, Agent, or Firm* — James S. Tak (57) ABSTRACT

A magnetically-induced SPME fiber actuation system includes a SPME fiber holder and a SPME fiber holder actuator, for holding and magnetically actuating a SPME fiber assembly. The SPME fiber holder has a plunger with a magnetic material to which the SPME fiber assembly is connected, and the magnetic SPME fiber holder actuator has an elongated barrel with a loading chamber for receiving the SPME fiber assembly-connected SPME fiber holder, and an external magnet which induces axial motion of the magnetic material of the plunger to extend/retract the SPME fiber from/into the protective needle of the SPME fiber assembly.

19 Claims, 6 Drawing Sheets

(56) References Cited

FOREIGN PATENT DOCUMENTS

| | | |
|---|---|---|
| WO | WO 2007/032039 | 3/2007 |
| WO | WO 2009/141797 A2 | 11/2009 |
| WO | WO 2013/011171 | 1/2013 |

OTHER PUBLICATIONS

Kohlert, C., G. Abel, et al. (2002) "Determination of thymol in human plasma by automated headspace solid-phase microextraction-gas chromatographic analysis." Journal of Chro.

* cited by examiner

MAGNETICALLY-INDUCED SOLID-PHASE MICROEXTRACTION FIBER ACTUATION SYSTEM FOR QUANTITATIVE HEADSPACE AND LIQUID SAMPLING

CROSS-REFERENCE TO RELATED APPLICATIONS

This application claims the benefit of U.S. provisional application No. 61/836,581 filed Jun. 18, 2013, which is incorporated by reference herein.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to solid-phase microextraction (SPME) devices and methods, and more specifically to a magnetically-induced SPME fiber actuation system and related devices for performing SPME fiber-based headspace and liquid sampling.

DESCRIPTION OF RELATED ART

Solid-phase microextraction (SPME) is a quantitative sampling technique that enables trace-level multi-analyte detection for a wide range of sample matrices and environmental conditions. In conventional SPME, a syringe-like device houses a retractable fused silica fiber with an immobilized stationary extraction phase at its tip, which is inserted into the sample headspace or liquid to collect and concentrate analytes via absorption and/or adsorption, until ideally equilibrium is achieved. At equilibrium the quantity of analytes extracted into the stationary phase is proportional to the concentration of analytes in the sample. Once the SPME fiber is removed from the sample, the analysis of the adsorbed analytes must be performed within minutes to hours to minimize analyte partitioning out of the stationary phase and the risk of contamination. Typically, the SPME collected analytes are desorbed into a gas chromatograph coupled to a mass analyzer (i.e. SPME-GC-MS) for separation and quantitation.

Some of the attributes of SPME include the following: the SPME fiber design combines extraction and enrichment into a single step, requiring typically only minutes to tens of minutes to perform; liquid solvents are not required since the stationary phase acts as a solid solvent; many different fiber coating choices are commercially available; SPME fibers are relatively inexpensive and can be used for months to years depending on the application; and the simplicity of the SPME fiber assembly allows for ease of manual use or automation (e.g. SPME-GC-MS). The conventional SPME technique has been widely adopted, and a variety of SPME related hardware is available including devices for preconditioning/reconditioning SPME fibers, for housing the SPME fiber when not in use, for manual or automated septum-based SPME sampling, and for transporting the SPME fiber (post sampling) to the analysis instrument (e.g. GC-MS).

Conventional SPME apparatuses and methods are known to have various limitations in different SPME sampling scenarios. For example, when SPME samplings are acquired away from the analysis instrument (e.g. GC-MS), as is typically the case for field measurements, there is a need to transport the preconditioned SPME fiber to the sample location, perform the measurement, and then transport the SPME fiber to an instrument for analysis, all without contaminating the fiber and before the collected analyte(s) partition out of the stationary phase. Prior art SPME devices for housing the SPME fiber may not be sufficiently airtight and therefore may be limited in their ability to prevent contamination. Even commercial SPME devices designated as field samplers and characterized as being completely sealed off from the environment require manual operation of a plunger during the sampling (i.e. not designed for sampling automation); the need to manually operate the device greatly limits its use in extremely hazardous environments because of the need to mitigate worker exposure. These field samplers are often capable of only using a single SPME fiber per measurement, which greatly limits the ability to extract the broadest range of possible analytes without potential losses of information on small classes of analytes such as, for example, polar compounds. Furthermore, there is no means for enabling the use of internal standards within the field sampler sealed-off device to correct for analyte competition or analyte mobility on the SPME fiber.

The need for SPME sampling involving extremely hazardous environments, or environments requiring sampling of very small volumes or very transient species (especially when the opportunity to access the headspace or liquid is extremely limited) is becoming more important for various industrial, environmental, military, and national security applications. However, the manual operation of commercial field sampling SPME devices can limit their use in such extreme or hazardous environments because of the need to mitigate worker exposure. Novel, simple, SPME sampling methods are needed to enable remote or automated operations (e.g. robot, landers, rovers, etc.) while promoting accuracy and reliability in SPME sampling.

SUMMARY

One aspect of the present invention includes a SPME fiber holder for holding a SPME fiber assembly of a type having a protective tube, a SPME fiber positioned inside the protective tube, and an end connector operably connected to the SPME fiber to actuate the SPME fiber between a retracted position in the protective tube and an extended position outside the protective tube, said SPME fiber holder comprising: a plunger having a magnetic material and adapted to connectably receive the end connector of the SPME fiber assembly; and a hollow cylinder having an open end, an opposite closed end with an aperture, and a chamber adapted to receive through the open end the SPME fiber assembly-connected plunger so that the protective tube extends out through the aperture, whereby the plunger may be actuated to extend/retract the SPME fiber from/into the protective tube by an off-device magnet which induces axial motion of the magnetic material of the plunger.

In addition, various embodiments of the SPME fiber holder may also include: wherein the plunger includes a guide pin, and the hollow cylinder has a keyed slot on a sidewall of the cylinder which is adapted to engage the guide pin so that the plunger is locked from axially translating relative to the cylinder while the SPME fiber is in the retracted position, is free to be axially translated relative to the cylinder, and is locked from axially translating relative to the cylinder while the SPME fiber is in the extended position; or wherein the plunger further includes a chamber-engaging section adapted to axially reciprocate in the chamber, and a shank extending from the chamber-engaging section to a handle end with the magnetic material located with the shank; or wherein the chamber-engaging section is a hollow cylindrical section with an open end adapted to receive the end connector therethrough to connect to the shank at an end connector connection location thereof; or wherein the plunger further includes a side aperture adjacent the end connector connection location for enabling access to the end connector when connecting or disconnecting from the shank; or wherein surfaces of the SPME fiber holder are passivated with a passivation surface treatment selected from the group consisting of electro polishing, metallic coating, dielectric coating, fused silica coating, and combinations thereof.

Another aspect of the present invention includes a magnetic SPME fiber holder actuator for magnetically actuating a SPME fiber holder of a type having a magnetic material operably connected to actuate a SPME fiber between a retracted position in a protective tube and an extended position outside the protective tube, said magnetic SPME fiber holder actuator comprising: an elongated barrel having a loading chamber, a loading end adapted to receive the SPME fiber assembly-connected SPME fiber holder into the loading chamber, and an opposite sampling end; a valve operably connected to control fluidic communication between the loading chamber and the sampling end; a removable cap adapted to connectably close the loading end after loading of the SPME fiber assembly-connected SPME fiber holder; a magnet operably connected to translate along a longitudinal axis of the elongated barrel for producing a magnetic field in the loading chamber which induces axial motion of the magnetic material to extend/retract the SPME fiber from/into the protective tube; and first and second stops positioned on the barrel on opposite sides of the magnet to define a travel range of the magnet, wherein the first stop is positioned so that when the magnet is stopped thereagainst, the loaded SPME fiber holder is induced to extend the SPME fiber from the protective tube, and the second stop is positioned so that when the magnet is stopped thereagainst, the loaded SPME fiber holder is induced to retract the SPME fiber from the protective tube.

In addition, various embodiments of the magnetic SPME fiber holder actuator may also include: wherein the first and second stops are magnetic materials; or wherein the first stop is positioned so that when the magnet is stopped thereagainst, the loaded SPME fiber holder is induced to extend the protective tube through the valve in an open position so that the SPME fiber extends beyond the valve; or further comprising at least one additional elongated barrel arranged substantially in parallel with the other barrel(s), each additional barrel having a loading chamber, a loading end adapted to receive another SPME fiber assembly-connected SPME fiber holder into the loading chamber, and an opposite sampling end fluidically connected to the other sampling end(s) of the other barrel(s) and the valve via a joint sampling housing; or wherein the magnet is operably connected to translate along and adjacent the longitudinal axes of the elongated barrels for producing a magnetic field in the loading chambers thereof; or wherein each of the first and second stops is positioned on the barrels on opposite sides of the magnet to define a travel range of the magnet; or further comprising at least one additional magnet operably connected to translate along the longitudinal axis of the at least one additional elongated barrel for producing a magnetic field in the loading chamber(s) thereof; or further comprising at least one additional set of first and second stops positioned on the at least one additional elongated barrel on opposite sides of the at least one additional magnet to define a travel range thereof; or further comprising an auxiliary port fluidically connected to the loading chamber; or wherein interior surfaces of the loading chamber are passivated with a passivation surface treatment selected from the group consisting of electro polishing, metallic coating, dielectric coating, fused silica coating, and combinations thereof.

Another aspect of the present invention includes a magnetically-induced SPME fiber actuation system for holding and magnetically actuating a SPME fiber assembly of a type having a protective tube, a SPME fiber positioned inside the protective tube, and an end connector operably connected to the SPME fiber to actuate the SPME fiber between a retracted position in the protective tube and an extended position outside the protective tube, said magnetically-induced SPME fiber actuation system comprising: a SPME fiber holder comprising: a plunger having a magnetic material and adapted to connectably receive the end connector of the SPME fiber assembly; and a hollow cylinder having an open end, an opposite closed end with an aperture, and a chamber adapted to receive through the open end the SPME fiber assembly-connected plunger so that the protective tube extends out through the aperture, whereby the plunger may be actuated to extend/retract the SPME fiber from/into the protective tube by an off-device magnet which induces axial motion of the magnetic material of the plunger; and a magnetic SPME fiber holder actuator for magnetically actuating the SPME fiber holder, said magnetic SPME fiber holder actuator comprising: an elongated barrel having a loading chamber, a loading end adapted to receive the SPME fiber assembly-connected SPME fiber holder into the loading chamber, and an opposite sampling end; a valve operably connected to control fluidic communication between the loading chamber and the sampling end; a removable cap adapted to connectably close the loading end after loading of the SPME fiber assembly-connected SPME fiber holder; a magnet operably connected to translate along a longitudinal axis of the elongated barrel for producing a magnetic field in the loading chamber which induces axial motion of the magnetic material to extend/retract the SPME fiber from/into the protective tube; and first and second stops positioned on the barrel on opposite sides of the magnet to define a travel range of the magnet, wherein the first stop is positioned so that when the magnet is stopped thereagainst, the loaded SPME fiber holder is induced to extend the SPME fiber from the protective tube, and the second stop is positioned so that when the magnet is stopped thereagainst, the loaded SPME fiber holder is induced to retract the SPME fiber from the protective tube.

In addition, various embodiments of the magnetically-induced SPME fiber actuation system may also include: further comprising at least one additional elongated barrel arranged substantially in parallel with the other barrel(s), each additional barrel having a loading chamber, a loading end adapted to receive another SPME fiber assembly-connected SPME fiber holder into the loading chamber, and an opposite sampling end fluidically connected to the other sampling end(s) of the other barrel(s) and the valve via a joint sampling housing; or wherein surfaces of the SPME fiber holder are passivated with a passivation surface treatment selected from the group consisting of electro polishing, metallic coating, dielectric coating, fused silica coating, and combinations thereof; or wherein interior surfaces of the loading chamber are passivated with a passivation surface treatment selected from the group consisting of electro polishing, metallic coating, dielectric coating, fused silica coating, and combinations thereof.

These and other implementations and various features and operations are described in greater detail in the drawings, the description and the claims.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION

Generally, the present invention is directed to a SPME fiber holder (i.e. a SPME fiber assembly holder) incorporated with magnetic material to enable magnet-induced actuation of a SPME fiber of a SPME fiber assembly connected to the holder; to a magnetic SPME fiber holder actuator utilizing a magnet to magnetically induce actuation of a SPME fiber holder sealed or otherwise enclosed in a chamber of SPME fiber holder actuator and in turn to actuate the SPME fiber operably connected to the SPME fiber holder; and finally to a magnetically-induced SPME fiber actuation system comprising both the SPME fiber holder and the magnetic SPME fiber holder actuator together. It is appreciated that "SPME fiber" commonly refers to a fused silica fiber with an immobilized stationary extraction phase at its tip. And "SPME fiber assembly" commonly refers to commercially available assemblies that have the SPME fiber with coating integrated with a syringe-like needle assembly. In particular, SPME fiber assemblies typically comprise a protective tube or needle, a SPME fiber positioned inside the protective tube, and an end connector or component operably connected to the SPME fiber such as by a thin connecting arm or wire to actuate the SPME fiber between a retracted position in the protective tube and an extended position outside the protective tube. Additionally, some SPME fiber assemblies may also have a resiliently-biasing coil spring positioned between the protective tube (or more particularly, against a wide base of the protective tube that is designed to seat the coil spring) and the end connector to exert a restoring force on the end connector when the SPME fiber is in the extended position.

The holder, actuator, and system of the present invention may be used for and in conjunction with, for example, conventional, offline, active and other SPME based approaches/techniques for sampling, in applications such as for example, headspace analysis, liquid analysis, gas analysis, etc. field sampling, hazardous environmental sampling, remote sampling, internal standard addition for field sampling, automated sampling, magnetic translational SPME sampling non-manually actuated SPME sampling, manually actuated SPME sampling. Additionally the present invention may also be used for various SPME-related functions such as for example housing/protecting the SPME fiber, preconditioning the SPME fiber, transporting to and from the sample location, and (optionally) interfacing with a manifold and/or analysis equipment or other devices.

SPME Fiber Holder

The SPME fiber holder is generally comprised of two main components: first, a plunger to which a SPME fiber assembly may be operably connected to actuate a SPME fiber of the SPME fiber assembly between a retracted position in a protective tube (e.g. needle) and an extended position outside of the protective tube; and second, a hollow cylinder in which at least a portion of the plunger may reciprocably actuate to extend or retract the SPME fiber from the protective tube. The plunger is adapted to connectably receive an end connector of the SPME fiber assembly, such as by providing a threaded bore to accept a threaded shank of an end connector of the SPME fiber assembly, or other fastening or connecting methods or devices. The plunger also includes a magnetic material, such as for example, a permanent magnet, a ferrous material, or other materials which exhibit some form of magnetism and either produce a magnetic field (i.e. a magnet) or is influenced (induced to move) by one. The magnetic material may be embedded or otherwise located with the plunger, so that the plunger may be actuated to extend/retract the SPME fiber from/into the protective tube by an off-device magnet which magnetically induces axial motion of the magnetic material of the plunger.

And the hollow cylinder generally has an open end, an opposite closed end with a small diameter aperture, and a chamber adapted to receive the SPME fiber assembly-connected plunger through the open end so that the protective tube extends out through the aperture. The hollow cylinder also has a keyed slot formed on a sidewall of the cylinder which is adapted to engage a guide pin on the plunger so that the guide pin may be moved into various sections of the keyed slot which affect the ability of the plunger to move relative to the hollow cylinder. The keyed slot of the hollow cylinder functions to control axial translation of the plunger, and in particular is adapted to perform three basic functions: first, to immobilize (or lock) the plunger from moving (axially translating) relative to the hollow cylinder while the SPME fiber is retracted in the protective tube to maintain the retraction of the SPME fiber within the protective tube, such as during transport or storage; second, to immobilize (or lock) the plunger from moving (axially translating) relative to the hollow cylinder while the SPME fiber is extended from the protective tube to maintain the extension of the SPME fiber, such as during SPME-GC-MS port injection and fiber pre-conditioning; and finally, to unlock and free the plunger to move relative to the hollow cylinder to allow it to be axially translated or held in a stationary position for retraction or extension of the SPME fiber.

Figure 1:
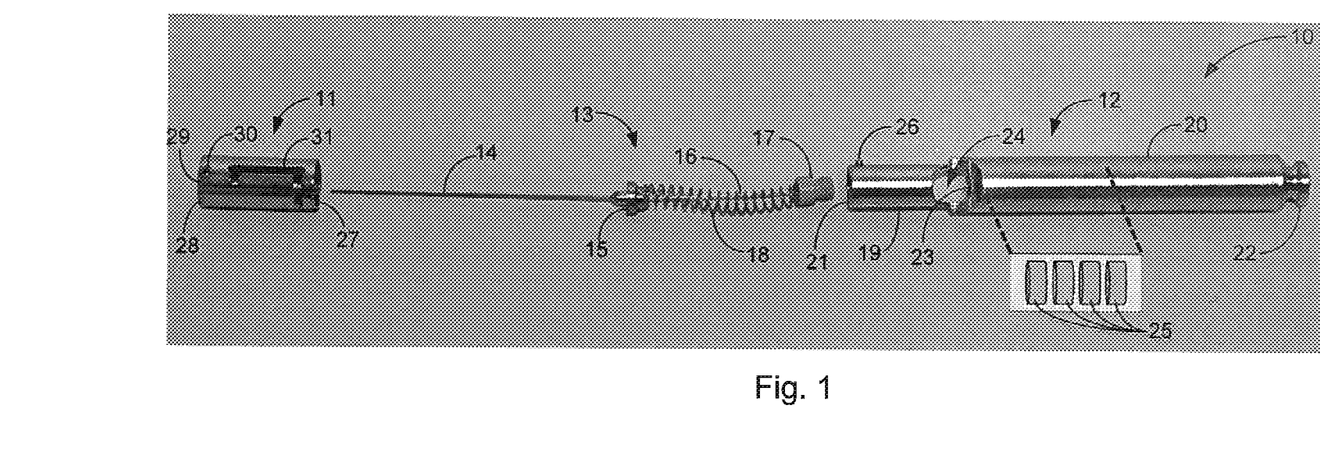
FIG. 1 is a photo showing an exploded view an example embodiment of the SPME fiber holder of the present invention, together with an example commercial SPME fiber assembly prior to loading and assembly.

Turning now to the drawings, FIG. 1 shows an exploded view of an example SPME fiber holder 10 of the present invention, generally comprising two main components, a hollow cylinder shown at reference character 11 and a plunger shown at reference character 12. A conventional SPME fiber assembly 13 is also shown in the exploded view to illustrate how it is loaded into the SPME fiber holder 10. As can be seen, the SPME fiber assembly 13 is shown having a protective tube or needle 14 in which a SPME fiber (not shown) is provided. The protective tube 14 is connected to a wide needle base 15 which operates as a seat for one end of coil spring 18. The SPME fiber in the protective tube is connected to a fiber actuating arm or wire 16 shown extending out from the needle 14, through the center of the coil spring 18, and connected to an end connector 17 shown with a threaded shank.

The hollow cylinder 11 is shown having a chamber, an open end 27 leading into the chamber, an opposite closed end 28 with an aperture 29 (for extending the needle therethroug), and a keyed slot 31 for guiding a guide pin 26 of the plunger 12. And the plunger 12 is shown having a chamber-engaging section 19 that is adapted to axially reciprocate in the chamber, and a shank section 20 extending from the chamber-engaging section to a handle end 22. The chamber-engaging section is particularly shown as a hollow cylindrical section with an open end 21 adapted to receive the end connector 17 therethrough to connect to the shank section at an end connector connection location 23 of the shank section. An access opening or side aperture 24 is shown located where the shank section 20 connects to the chamber-engaging section 26 and adjacent the end connector connection location 23, to enable access to the end connector 17 enabling access to the end connector when connecting or disconnecting from the shank. The guide pin 26 is also shown provided on the chamber-engaging section 19 of the plunger for controlling the motion of the plunger 12 relative to the hollow cylinder 11. The shank section also includes magnetic material 25 which may for example be housed or embedded inside the shank section or otherwise located with the shank section. The shank section may be constructed form a non-magnetic material (e,g. stainless steel) or a suitably weak magnetic material.

Figure 2:
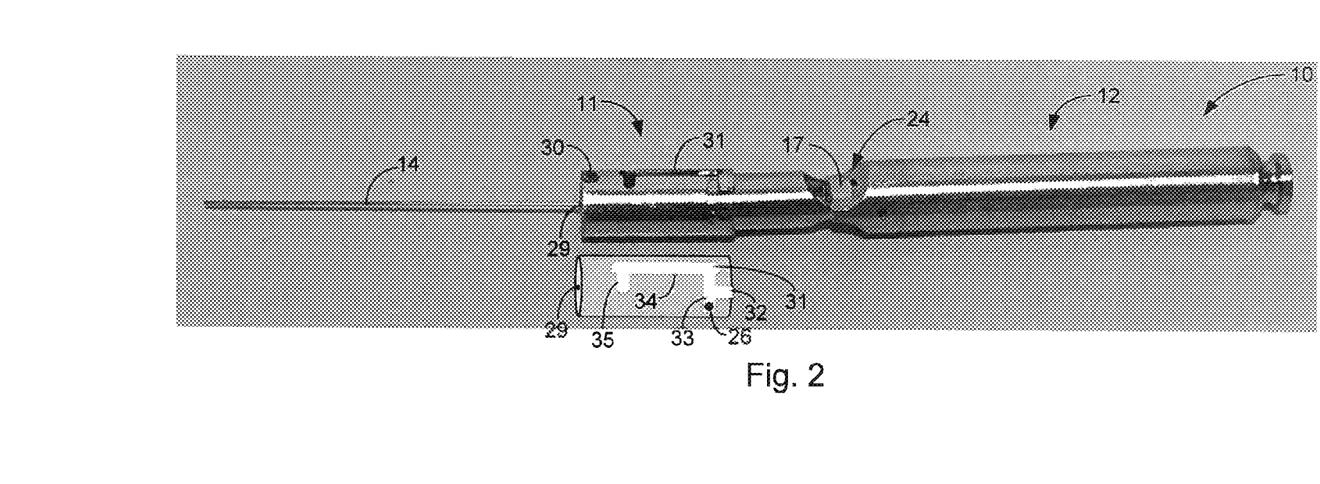
FIG. 2 is a photo showing the example embodiment of FIG. 1 assembled with the SPME fiber assembly loaded inside in a fully retracted position, and with the guide pin positioned in the keyed slot to lock translation of the plunger relative to the cylinder.
Figure 3:
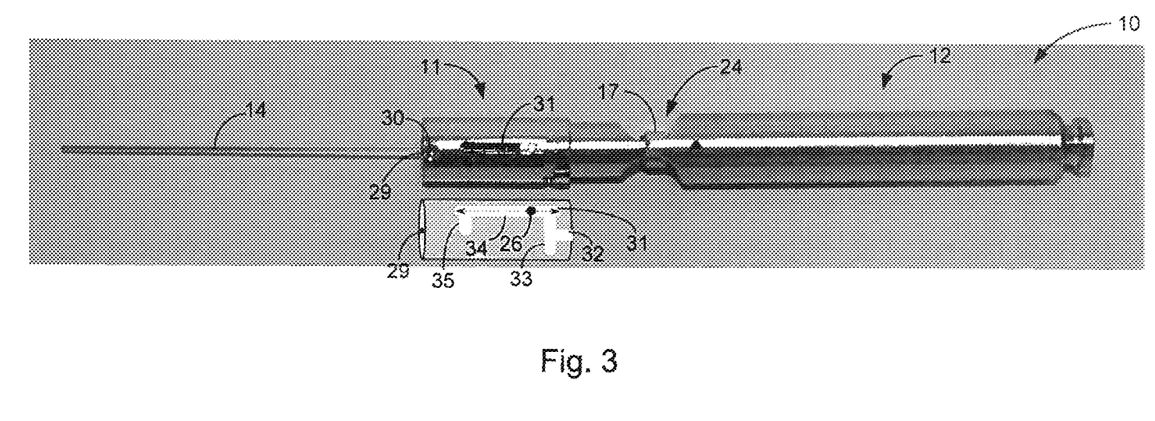
FIG. 3 is a photo following FIG. 2 with the guide pin positioned in the keyed slot to enable axial movement and actuation of the plunger, relative to the cylinder, to thereby enable extension and retraction of a SPME fiber.
Figure 4:
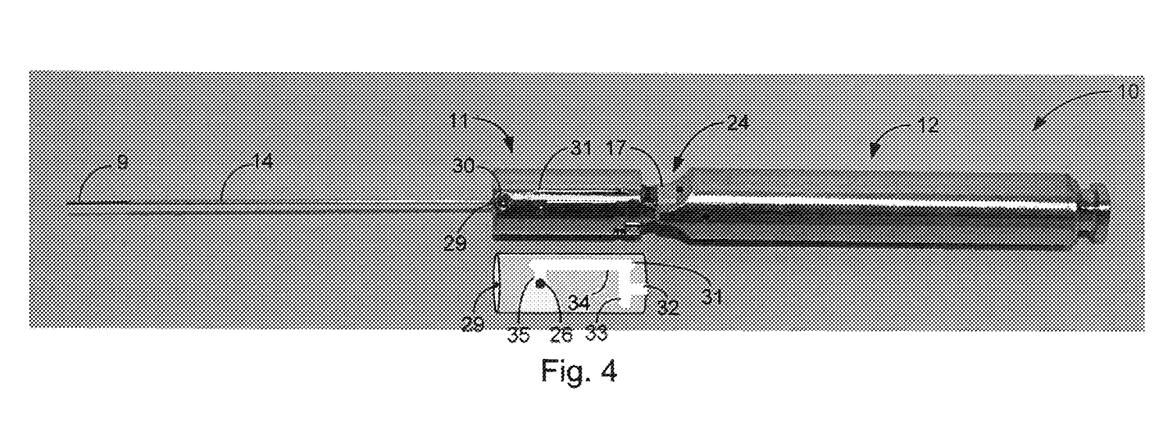
FIG. 4 is a photo following FIG. 3 with the guide pin positioned in the keyed slot to lock translation of the plunger relative to the cylinder while the SPME fiber is in the fully extended position outside of the protective tube.

FIGS. 2-4 show the hollow cylinder 11 and the plunger 12 assembled with the SPME fiber assembly loaded therein, and can be seen by the extension of the needle 14 through aperture 29, and the presence of the end connector 17 as viewable through the access opening 24. In particular, FIGS. 2-4 illustrate how the keyed slot 31 controls the ability of the plunger 12 to move relative to the cylinder 11. For clarity of the various guide pin 26 positions in the keyed slot, schematic illustrations are provided below the cylinder in each of the FIGS. 2-4. The keyed slot is shown formed on the cylinder sidewall with a shape resembling an end bracket ']', and having a slot entrance 32 for receiving the guide pin into the slot, followed by a first locking segment 33 oriented transverse to a longitudinal axis of the cylinder, followed by an axial slot segment 34, and then followed by a second locking segment 35 also oriented transverse to the longitudinal axis of the cylinder. As shown in FIG. 2, when the guide pin is positioned in the first locking segment 33 this prevents relative motion between the plunger and the cylinder along the longitudinal axis while the SPME fiber is in a non-deployed retracted position. As shown in FIG. 3, when the guide pin is positioned in the axial slot segment 34, the plunger is free to translate in an axial direction relative to the cylinder, and the SPME fiber may be either extended from or retracted into the protective tube. And as shown in FIG. 4, when the guide pin is positioned in the second locking segment 35 of the keyed slot, the plunger is again locked from axially translating relative to the cylinder, but this time while the SPME fiber is in the extended position. The plunger guide pin may also be positioned in this second locking segment (to compress the coil spring) before securing the hollow cylinder to the base (15 in FIG. 1) of the needle 14 via a set screw 30.

Magnetic SPME Fiber Holder Actuator

Once assembled and loaded with a SPME fiber assembly, the SPME fiber holder is ready for loading into the magnetic SPME fiber holder actuator. The magnetic SPME fiber holder actuator is an airtight (including up to high pressures, e.g. pressures greater than 100 psi) and vacuum compatible (including low pressures, e.g. pressures in the $10^{-3}$ to $10^{-7}$ Torr range) device designed to house the SPME fiber holder during any number of including but not limited to conventional SPME, offline SPME, and active SPME measurements; the sealed holder can also be used for transporting the SPME fiber hardware, as one example to the analysis instrument (e.g. GC-MS). The magnetic SPME fiber holder actuator generally comprises an elongated barrel having a loading chamber, a loading end adapted to receive the SPME fiber assembly-connected SPME fiber holder into the loading chamber (as indicated by dashed line 50), and an opposite sampling end. A valve is operably connected to control fluidic communication between the loading chamber and the sampling end, and a removable cap is adapted to connectably close the loading end after a SPME fiber assembly-connected SPME fiber holder is loaded. The holder actuator also includes a magnet which is operably connected to translate along a longitudinal axis of the elongated barrel, for producing a magnetic field in the loading chamber which induces axial motion of the magnetic material of the plunger to extend/retract the SPME fiber from/into the protective tube. Axial movement of the magnet is delimited by first and second stops positioned on the barrel on opposite sides of the magnet which defines a travel range of the magnet. In particular, the first stop is positioned so that when the magnet is stopped against it, the loaded SPME fiber holder is induced to extend the SPME fiber from the protective tube, and the second stop is positioned so that when the magnet is stopped against it, the loaded SPME fiber holder is induced to retract the SPME fiber from the protective tube. It is appreciated that the magnet is a sufficiently high strength magnet producing a magnetic field which induces movement of the magnetic material of the plunger. For example, Applicants have used neodymium iron boron disc-shaped magnets.

Figure 5:
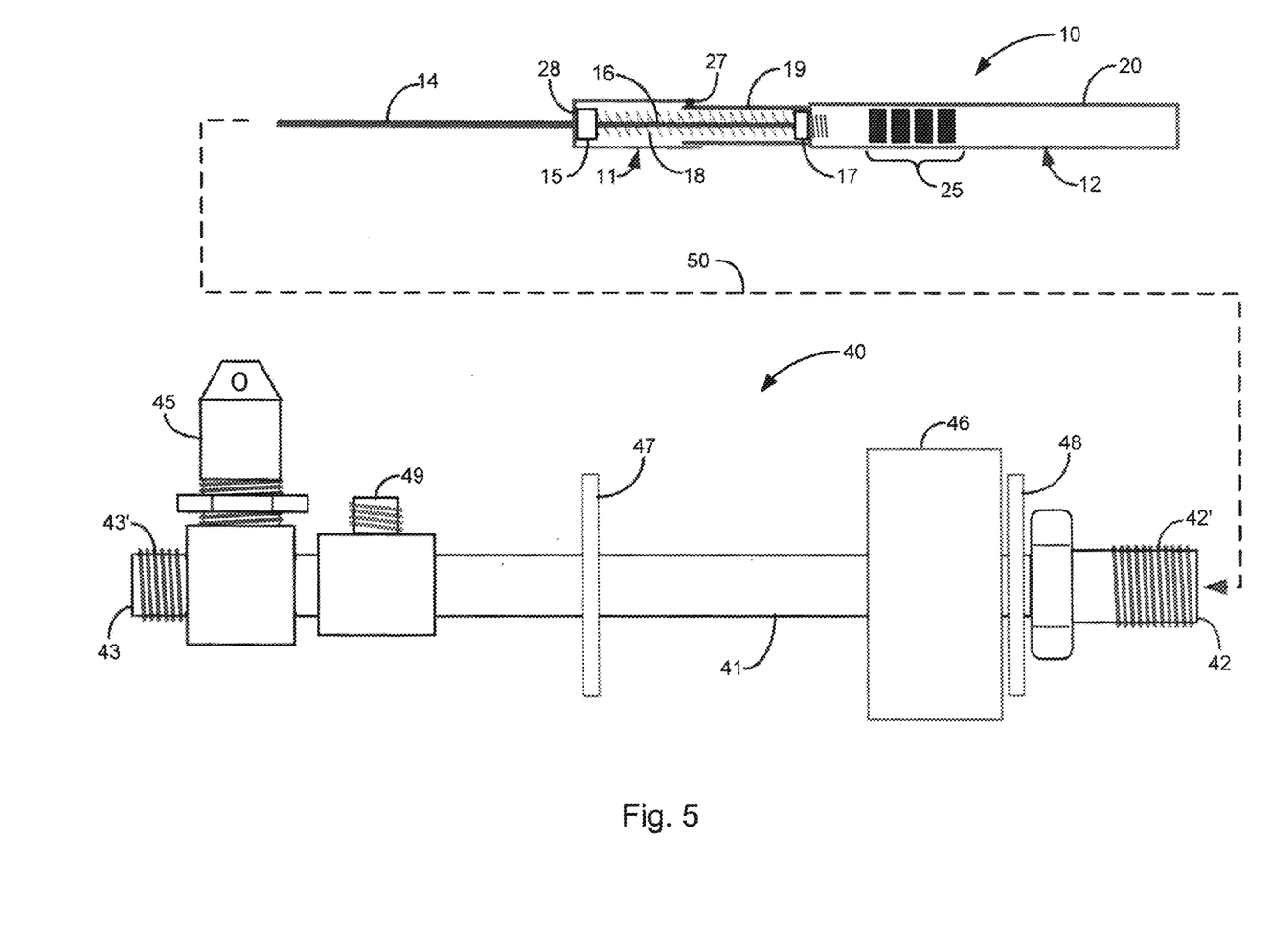
FIG. 5 shows a schematic view of an example embodiment of the magnetic SPME fiber holder actuator of the present invention, together with a schematic view of the example embodiment of the SPME fiber holder of FIGS. 1-4, to illustrate an example magnetically-induced SPME fiber actuation system of the present invention.

FIG. 5 shows a schematic view of an example embodiment of the magnetic SPME fiber holder actuator of the present invention, generally indicated at 40, together with a schematic view of the example embodiment of the SPME fiber holder 10 of FIGS. 1-4, to illustrate an example magnetically-induced SPME fiber actuation system of the present invention. The holder actuator 40 is shown having a rigid elongated barrel or tube 41 (e.g. stainless steel) extending between an open loading end 42 and an open sampling end 43. Both the loading end and the sampling end may be adapted (e.g. shown threaded at 42' and 43', respectively) to attach various types of fittings and interconnects to enable quick connection to other devices and systems, such as for example GC-MS analyzers, pre-conditioners, IS sources, purge and evacuation devices, etc. A removable cap (e.g. 44 in FIG. 6) is used to close the loading end 42 after the SPME fiber assembly-connected SPME fiber holder 10 is loaded. And a valve 45 is provided near the sampling end 43 to control fluidic communication through the sampling end.

FIG. 5 also shows a cylindrical (outer) magnet 46 operably connected to (e.g, slidably mounted on) the barrel or tube 4lso as to be translatable along a longitudinal axis of the barrel between two stops, a first stop 47 positioned between the magnet and the sampling end, and a second stop 48 positioned between the magnet and the loading end, The magnet produces a magnetic field in the loading chamber which induces axial motion of the magnetic material to extend/retract the SPME fiber from/into the protective tube. And the first and second stops are positioned on the barrel on opposite sides of the magnet to define a travel range of the magnet. In particular, the first stop is positioned so that when the magnet is stopped against it, the loaded SPME fiber holder is induced to extend the SPME fiber from the protective tube. And the second stop is positioned so that when the magnet is stopped against it, the loaded SPME fiber holder is induced to retract the SPME fiber into the protective tube. Magnetic materials may be used for the first and second stops which attract the magnet to each, to maintain the magnet's position adjacent each of the stops.

An auxiliary port 49 is also shown provided on the barrel 41 and in fluidic communication with the loading chamber of the barrel. The auxiliary port may be any one of but not limited to a valve, a quick disconnect type valve, septum, or septum-less device. A port could have multiple uses such as, any one of but not limited to, internal standard addition, purging and/or evacuating the device, adding a diagnostic such as a temperature or pressure sensor, or for use in extracting a sample from the internal atmosphere of the device such as with an autosampler. It is appreciated that the port may be a sealable port, double valved, etc., and may be a septum for use with an autosampler connected to an analyzer for direct sampling of the loading chamber housing the SPME fiber holder and SPME fiber assembly. In the alternative, the port may also be used with a septum-less device, such as a Merlin microseal which requires the use of a specific gauge SPME needle to allow the needle to enter while maintaining a leak-free seal. These types of septumless ports typically utilize a protective cap, which is manually screwed onto threads on the device when not in use.

The magnetic SPME fiber holder actuator can serve as an extended storage vessel for analytes extracted onto the SPME fiber of the SPME fiber assembly-coupled SPME fiber holder, enabling on-site sampling without the need for a sample analyzer at each sampling location. In some instances it may be desirable or even necessary to passivate the interior surfaces of the magnetic SPME fiber holder actuator, as well as surfaces of the SPME fiber holder, to mitigate the risk of analytes desorbing from the SPME fiber and preferentially absorbing/adsorbing to the magnetic SPME fiber holder actuator internal surfaces and SPME fiber holder surfaces. Passivation techniques for various material surfaces could include, but are not limited to, electro polishing; gold plating; chemical vapor deposition of fused silica; and combination thereof. Because the quantity of analyte extracted onto the SPME fiber is proportional to the concentration in the original sample (assuming the condition of equilibrium was achieved during the original sampling), it is essential to maintain the SPME fiber sample integrity during storage, extended or otherwise, until the SPME fiber contents are analyzed.

Magnetically-Induced SPME Fiber Actuation

Figure 6:
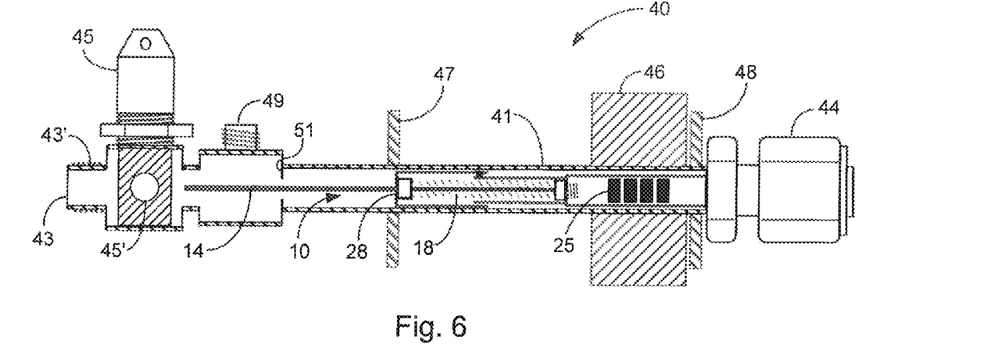
FIGS. 6-8 show three progressive views of the magnetic actuation of the SPME fiber holder of FIG. 5 induced by axially translating the magnet of the magnetic SPME fiber holder actuator of FIG. 5, with FIG. 6 showing the magnet in a first position to magnetically induce the SPME fiber to a fully retracted position, with FIG. 7 showing the magnet in a second position to magnetically induce the needle to a fully extended position but prior to fully extending the SPME fiber out therefrom, and with FIG. 8 showing the magnet in a third position to magnetically induce the SPME fiber to a fully extended position.
Figure 7:
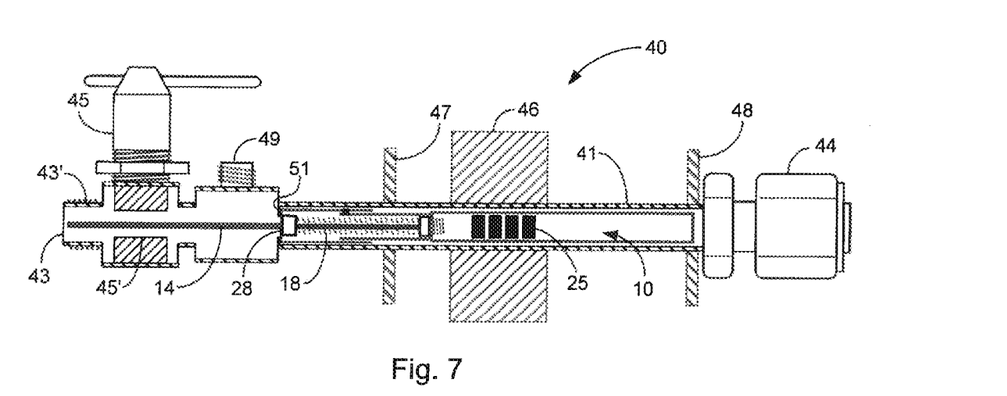
Figure 8:
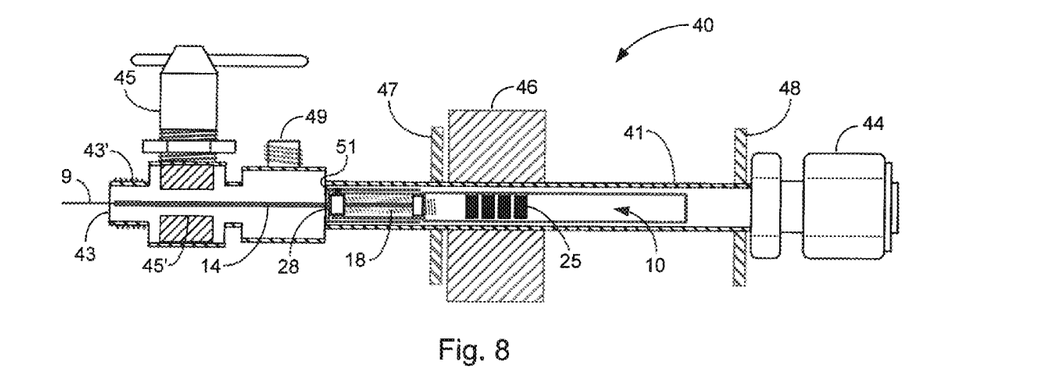

FIGS. 6-8 show three progressive views of the magnetic actuation of the SPME fiber holder of FIG. 5 induced by axially translating the magnet of the magnetic SPME fiber holder actuator of FIG. 5. As can he seen in all three of FIGS. 6-8, the position of the magnetic material 25 of the plunger is determined by the position of the magnet 46 due to the strong attraction between the magnet and the magnetic material. And since the plunger position determines the actuation of the SPME fiber, it is appreciated that the position of the magnet 46 also determines the position and actuation of the SPME fiber, In particular, FIG. 6 shows the magnet 46 positioned adjacent stop 48 which enables holder 10 to be loaded into the barrel without compressing the spring 18 (since the closed end 28 of the hollow cylinder is not pressed against internal stop 51 shown in FIGS. 6-7 as a radish inward directed annular shoulder or wall) or risking contact between the needle 14 and closed valve 45 as represented by the orientation of valve aperture 45'. FIG. 7 shows the magnet 46 in a second position away from stop 48 and approaching stop 47, with the magnetic material 25 of the plunger also repositioned adjacent the magnet due to the magnetic attraction between the magnet 46 and magnetic material 25 which induced forward translation toward the sampling end of the barrel. In this position, the coil spring has begun to compress (i,e, the SPME fiber has begun to extend down the protective tube 14) and the closed end 28 is shown abutted against internal stop 51 so that the needle is extended to its maximum extension beyond and passed the open valve 45. During SPME sampling, the valve 45 must he opened prior to moving the outer magnet 46 forward resulting in translation of the plunger, translation of the needle, beginning compression of the SPME fiber assembly spring, and beginning extension of the SPME fiber. And FIG. 8 shows the magnet 46 in a third position adjacent the stop 47 to magnetically induce the SPME fiber to a fully extended position. When the outer magnet is translated to the forward stop, the SPME fiber assembly spring is compressed resulting in extension of the SPME fiber from the protective needle. It is appreciated that the valve must be in the open position before the SPME fiber is extended for sampling, otherwise, the fiber may be damaged.

Multi-Barrel Embodiments

Figure 9:
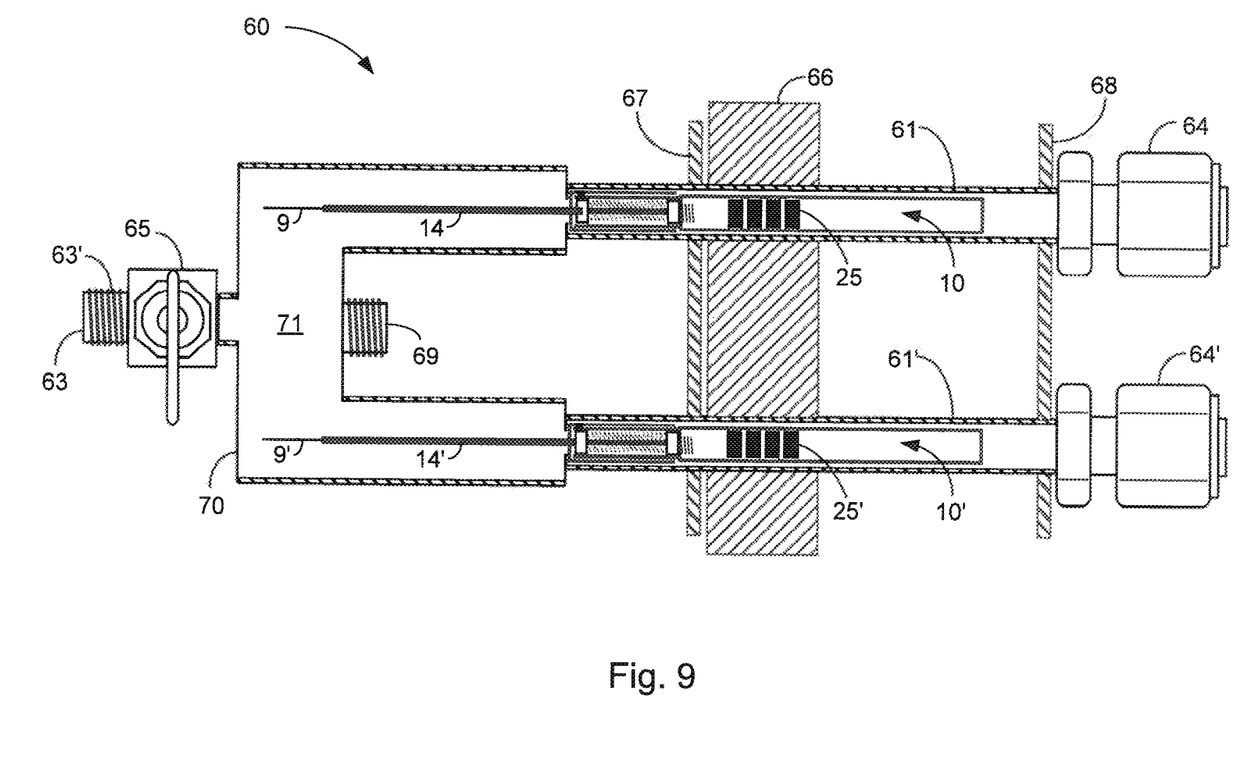
FIG. 9 shows another example embodiment of the magnetic SPME fiber holder actuator of the present invention, having two barrels for loading and simultaneously actuating two SPME fiber holders with a single magnet.
Figure 10:
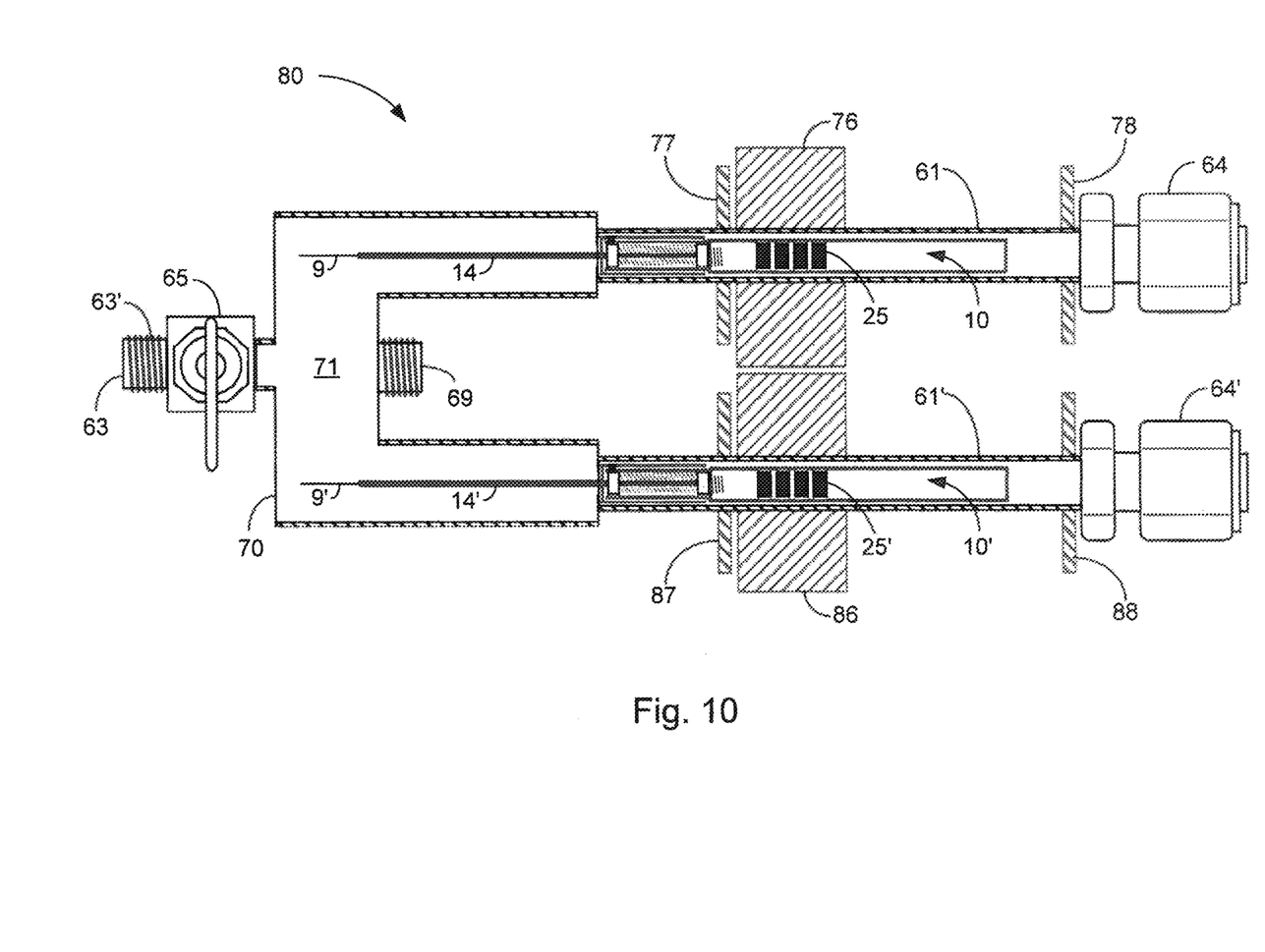
FIG. 10 shows another example embodiment of the magnetic SPME fiber holder actuator of the present invention, having two barrels for loading and independently actuating two SPME fiber holders with two independently moveable magnets.

FIGS. 9 and 10 show two example embodiments having multiple barrels for actuation multiple SPME fiber holders either simultaneously or independently. Multiple units capable of simultaneous or independent sampling, would enable the extraction of a broad range of possible analytes without potential losses of information on small classes of analytes such as polar molecules. Generally, at least one additional elongated barrel is provided and arranged substantially in parallel with the other barrel(s), with each additional barrel having a loading chamber, a loading end adapted to receive another SPME fiber assembly-connected SPME fiber holder into the loading chamber, and an opposite sampling end fluidically connected to the other sampling end(s) of the other barrel(s) and the valve via a joint sampling housing surrounding a sampling space. The sampling space is itself fluidically connected to a sampling port via the valve and enables the simultaneous use/sampling of more than one SPME fiber assembly, the addition of internal standards, the ability to precondition the SPME fiber while housed within the magnetic translational fiber holder, and combinations thereof. It is appreciated in this arrangement that during SPME sampling, the valve does not require opening prior to moving the outer magnet forward, resulting in translation of the SPME fiber hardware, compression of the SPME fiber assembly spring, and extension of the SPME fiber into the sampling space, since the SPME fiber will fully extend only into the sampling space and not through the valve.

FIG. 9 shows a first example multi-barrel embodiment at reference character 60 having barrels 61 and 61' arranged substantially parallel to each other and shown loaded with two SPME fiber holders 10 and 10'. While the loading ends (shown closed with caps 64 and 64') are independent of each other, a single sampling port 63 is shown provided and in fluidic communication with both barrels arid holders via joint sampling housing 70 enclosing a sampling space 71 where both needles 14 and 14' may be extended into, as well as the corresponding SPME fibers 9 and 9'. As shown in FIG. 9 a single magnet 66 is operably connected to translate along and adjacent the longitudinal axes of both of the elongated barrels 61 and 61' for producing a magnetic field in the loading chambers thereof. And only a single pair of first and second stops 67 and 68 are provided and positioned on both barrels on opposite sides of the magnet to define a travel range of the magnet. This arrangement enables simultaneous actuation and sampling using SPME fibers in both barrels. An auxiliary port 69 is also shown connected to the joint sampling housing 70. And as previously discussed, the auxiliary port may be any one of but not limited to a valve, a quick disconnect type valve, septum, or septum-less device.

In contrast to FIG. 9, FIG. 10 shows a second example multi-barrel embodiment at reference character 80 having barrels 61 and 61' arranged substantially parallel to each other and shown loaded with two SPME fiber holders 10 and 10', similar to FIG. 9. While the loading ends (shown closed with caps 64 and 64') are independent of each other, a single sampling port 63 is shown provided and in fluidic communication with both barrels and holders via a joint sampling housing 70 enclosing a sampling space 71 where both needles 14 and 14' may be extended into, as well as the corresponding SPME fibers 9 and 9'. In contrast to FIG. 9, however, each barrel 61 and 61' has its own magnet 76 and 86, respectively, operably connected to independently translate along and adjacent the longitudinal axes of the respective elongated barrels 61 and 61' for producing separate magnetic fields in the loading chambers thereof. And two pairs of first and second stops, 77, 78, and 87, 88 are provided and positioned on each of the barrels on opposite sides of the magnet to define a corresponding travel range of the magnet. This arrangement enables independent actuation and sampling of SPME fibers loaded in both barrels. It is appreciated that a septum or other seal may be internally provided, such as at the inner stop where the closed end of the hollow cylinder abuts against, to prevent exposure of either SPME fiber until being independently actuated to pierce the septum and into the sampling space.

Although the description above contains many details and specifics, these should not be construed as limiting the scope of the invention but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art. In the claims, reference to an element in the singular is not intended to mean "one and only one" unless explicitly so stated, but rather "one or more," All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

We claim:

1. A SPME fiber holder for holding a SPME fiber assembly of a type having a protective tube, a SPME fiber positioned inside the protective tube, and an end connector operably connected to the SPME fiber to actuate the SPME fiber between a retracted position in the protective tube and an extended position outside the protective tube, said SPME fiber holder comprising:

a plunger having a chamber-engaging section adapted to connectably receive the end connector of the SPME fiber assembly, and a shank section extending from the chamber-engaging section to a handle end and including a magnetic material; and a hollow cylinder having an open end, an opposite closed end with an aperture, and a chamber adapted to receive the chamber-engaging section of the plunger through the open end so that the protective tube of a SPME fiber assembly connected to the chamber-engaging section extends out through the aperture and the magnetic material remains outside the hollow cylinder, wherein the plunger is actuable by an actuator magnet whose motion along a longitudinal axis of the hollow cylinder induces a corresponding axial motion of the magnetic material of the plunger relative to the hollow cylinder to extend/retract the SPME fiber from/into the protective tube.

2. The SPME fiber holder of claim 1, wherein the plunger includes a guide pin, and the hollow cylinder has a keyed slot on a sidewall of the cylinder which is adapted to engage the guide pin so that the plunger is locked from axially translating relative to the cylinder while the SPME fiber is in the retracted position, is free to be axially translated relative to the cylinder, and is locked from axially translating relative to the cylinder while the SPME fiber is in the extended position.

3. The SPME fiber holder of claim 1, wherein the chamber-engaging section is a hollow cylindrical section with an open end adapted to receive the end connector therethrough to connect to the shank section at an end connector connection location thereof.

4. The SPME fiber holder of claim 3, wherein the plunger further incudes a side aperture adjacent the end connector connection location for enabling access to the end connector when connecting or disconnecting from the shank section.

5. The SPME fiber holder of claim 1, wherein surfaces of the SPME fiber holder are passivated with a passivation surface treatment selected from the group consisting of electro polishing, metallic coating, dielectric coating, fused silica coating, and combinations thereof.

6. A magnetic SPME fiber holder actuator for magnetically actuating a SPME fiber holder of a type having a magnetic material operably connected to actuate a SPME fiber between a retracted position in a protective tube and an extended position outside the protective tube, said magnetic SPME fiber holder actuator comprising:

an elongated barrel having a loading chamber, a loading end adapted to receive the SPME fiber assembly-connected SPME fiber holder into the loading chamber, and an opposite sampling end;

a valve operably connected to control fluidic communication between the loading chamber and the sampling end;

a removable cap adapted to connectably close the loading end after loading of the SPME fiber assembly-connected SPME fiber holder;

a magnet operably connected to translate along a longitudinal axis of the elongated barrel for producing a magnetic field in the loading chamber which induces axial motion of the magnetic material to extend/retract the SPME fiber from/into the protective rube; and first and second stops positioned on the barrel on opposite sides of the magnet to define a travel range of the magnet, wherein the first stop is positioned so that when the magnet is stopped thereagainst, the loaded SPME fiber holder is induced to extend the SPME fiber from the protective tube, and the second stop is positioned so that when the magnet is stopped thereagainst, the loaded SPME fiber holder is induced to retract the SPME fiber from the protective tube.

7. The magnetic SPME fiber holder actuator of claim 6, wherein the first and second stops are magnetic materials.

8. The magnetic SPME fiber holder actuator of claim 6, wherein the first stop is positioned so that when the magnet is stopped thereagainst, the loaded SPME fiber holder is induced to extend the protective tube through the valve in an open position so that the SPME fiber extends beyond the valve.

9. The magnetic SPME fiber holder actuator of claim 6, further comprising at least one additional elongated barrel(s) arranged substantially in parallel with said elongated barrel, each of the at least one additional elongated barrel(s) having a loading chamber, a loading end adapted to receive another SPME fiber assembly-connected SPME fiber holder into the loading chamber, and an opposite sampling end fluidically connected to the sampling end of said elongated barrel and the valve via a joint sampling housing.

10. The magnetic SPME fiber holder actuator of claim 9, wherein the magnet is operably connected to translate along and adjacent the longitudinal axes of said elongated barrel and the at least one additional elongated barrel(s) for producing a magnetic field in the loading chambers thereof.

11. The magnetic SPME fiber holder actuator of claim 10, wherein each of the first and second stops is positioned on the barrels on opposite sides of the magnet to define a travel range of the magnet.

12. The magnetic SPME fiber holder actuator of claim 9, further comprising at least one additional magnet operably connected to translate along the longitudinal axis of the at least one additional elongated barrel(s) for producing a magnetic field in the loading chamber(s) thereof.

13. The magnetic SPME fiber holder actuator of claim 12, further comprising at least one additional set of first and second stops positioned on the at least one additional elongated barrel(s) on opposite sides of the at least one additional magnet to define a travel range thereof.

14. The magnetic SPME fiber holder actuator of claim 6, further comprising an auxiliary port fiuidically connected to the loading chamber.

15. The magnetic SPME fiber holder actuator of claim 6, wherein interior surfaces of the loading chamber are passivated with a passivation surface treatment selected from the group consisting of electro polishing, metallic coating, dielectric coating, fused silica coating, and combinations thereof.

16. A magnetically-induced SPME fiber actuation system for holding and magnetically actuating a SPME fiber assembly of a type having a protective tube, a SPME fiber positioned inside the protective tube, and an end connector operably connected to the SPME fiber to actuate the SPME fiber between a retracted position in the protective tube and an extended position outside the protective tube, said magnetically-induced SPME fiber actuation system comprising:

a SPME fiber holder comprising: a plunger haying a chamber-engaging section adapted to connectably receive the end connector of the SPME fiber assembly, and a shank section extending from the chamber-engaging section to a handle end and including a magnetic material; and a hollow cylinder having an open end, an opposite closed end with an aperture, and a chamber adapted to receive the chamber-engaging section of the plunger through the open end so that the protective tube of a SPME fiber assembly connected to the chamber-engaging section extends out through the aperture and the magnetic material remains outside the hollow cylinder, wherein the plunger is actuable by an actuator magnet whose motion along a longitudinal axis of the hollow cylinder induces a corresnonding axial motion of the magnetic material of the plunger relative to the hollow cylinder to extend/retract the SPME fiber from/into the protective tube; and a magnetic SPME fiber holder actuator for magnetically actuating the SPME fiber holder, said magnetic SPME fiber holder actuator comprising: an elongated barrel having a loading chamber, a loading end adapted to receive the SPME fiber assembly-connected SPME fiber holder into the loading chamber, and an opposite sampling end; a valve operably connected to control fluidic communication between the loading chamber and the sampling end; a removable cap adapted to connectably close the loading end after loading of the SPME fiber assembly-connected SPME fiber holder; a magnet operably connected to translate along a longitudinal axis of the elongated barrel for producing a magnetic field in the loading chamber which induces axial motion of the magnetic material to extend/retract the SPME fiber from/into the protective tube; and first and second stops positioned on the barrel on opposite sides of the magnet to define a travel range of the magnet, wherein the first stop is positioned so that when the magnet is stopped thereagainst, the loaded SPME fiber holder is induced to extend the SPME fiber from the protective tube, and the second stop is positioned so that when the magnet is stopped thereagainst, the loaded SPME fiber holder is induced to retract the SPME fiber from the protective tube.

17. The magnetically-induced SPME fiber actuation system of claim 16, wherein the magnetic SPME fiber holder actuator further comprises at least one additional elongated barrel(s) arranged substantially in parallel with the other barrel, each of the at least one additional elongated barrel(s) having a loading chamber, a loading end adapted to receive another SPME fiber assembly-connected SPME fiber holder into the loading chamber, and an opposite sampling end fluidically connected to the sampling end of said elongated barrel and the valve via a joint sampling housing.

18. The magnetically-induced SPME fiber actuation system of claim 16, wherein surfaces of the SPME fiber holder are passivated with a passivation surface treatment selected from the group consisting of electro polishing, metallic coating, dielectric coating, fused silica coating, and combinations thereof.

19. The magnetically-induced SPME fiber actuation system of claim 16, wherein interior surfaces of the loading chamber are passivated with a passivation surface treatment selected from the group consisting of electro polishing, metallic coating, dielectric coating, fused silica coating, and combinations thereof.

* * * * *